(12) United States Patent
Ostermaier

(10) Patent No.: US 6,331,651 B1
(45) Date of Patent: Dec. 18, 2001

(54) PROCESS FOR MAKING HEXAMETHYLENE DIAMINE USING OZONE-TREATED ADIPONITRILE THAT CONTAINS PHOSPHOROUS COMPOUNDS

(75) Inventor: John Joseph Ostermaier, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/839,808

(22) Filed: Apr. 20, 2001

Related U.S. Application Data

(63) Continuation-in-part of application No. 09/664,569, filed on Sep. 18, 2000.

(51) Int. Cl.$^7$ .................................................. C07C 209/48
(52) U.S. Cl. ............................................ 564/490; 564/498
(58) Field of Search ...................................... 564/490, 498

(56) References Cited

FOREIGN PATENT DOCUMENTS

672712 * 10/1963 (CA) ................................ 260/465.8

* cited by examiner

*Primary Examiner*—Johann Richter
*Assistant Examiner*—Brian J. Davis

(57) ABSTRACT

A process for making HMD in which a butadiene hydrocyantion reaction product that contains phosphorous-containing impurities is treated with ozone.

2 Claims, No Drawings ations is a continuation-in-part of U.S. application Ser. No. 09/664,569, filed Sep. 18, 2000.

PROCESS FOR MAKING HEXAMETHYLENE DIAMINE USING OZONE-TREATED ADIPONITRILE THAT CONTAINS PHOSPHOROUS COMPOUNDS

RELATED APPLICATION

This application is a continuation-in-part of U.S. application Ser. No. 09/664,569, filed Sep. 18, 2000.

BACKGROUND ART

It is known that hexamethylene diamine (HMD) can be made by a process in which butadiene is hydrocyanated in the presence of a nickel catalyst to yield a reaction product that contains adiponitrile (ADN), and the ADN is hydrogenated using an iron-containing catalyst to yield a reaction product that contains HMD.

It is also known that the hydrocyanation step can be carried out in the presence of certain phosphorous-containing promoter compounds, such as tritolyl phosphite (TTP) and the more recently described monodentate and bidentate compounds. U.S. Pat. Nos. 3,496,215; 3,496,217; 3,496,218; 5,512,695; 5,512,696; 5,523,453; 5,663,369; 5,693,843; 5,723,641; and 5,821,378 describe some of these monodentate and bidentate compounds.

The hydrocyanation step can lead to the production of certain impurities, such as 2-cyanocyclopentylideneimine, which are difficult to separate from the ADN by distillation. One way to address this problem is to treat the ADN-containing hydrocyanation reaction product with ozone to convert the impurities to more easily separable compounds. The ozone treated hydrocyanation reaction product can then be purified by standard industrial methods such as dehydration and distillation. See Canadian Patent 672,712.

Published International Patent Applications WO 00/03972 and 00/12460 describe methods for producing HMD in which ADN is hydrogenated to yield a reaction product that contains unreacted ADN, HMD and aminocapronitrile (ACN). The HMD and ACN are separated from the reaction product, and unreacted ADN is returned to the hydrogenation reactor. The unreacted ADN can be treated, if desired, with ozone, among others.

Published German patent application DE 19636765 A1 (1998) describes processes for removing phosphorus-containing compounds from ADN made by the hydrocyantion of butadiene. These processes are said to be useful for decreasing the deactivation of iron-based catalysts which are used to hydrogenate the ADN. These processes involve distillation of the ADN, extraction of the ADN, treatment of the ADN with base, and treatment of the ADN using adsortpion or chemisorption.

Iron is a known catalyst for, among other things, the synthesis of ammonia, which is a process that is said to be closely related to hydrogenation. Phosphorous is a known catalyst poison, although it may be possible to detoxify phosphorous by chemically bonding it to other elements to produce a so-called shielded structure in which there are no unshared electron pairs. See Maxted, E. B., The Poisoning of Metallic Catalysts, Advances in Catalysis, Vol. III, p 129, Academic Press, 1951.

It is known that ozone can attack nucleophilic phosphorous. In particular, it is known that ozone can react with triphenylphosphine to produce the corresponding oxide in good yield. See Bailey, P. S., Ozonation in Organic Chemistry, Vol. II, p 201, Academic Press, 1982.

The use of phosphorous-containing ligands in hydrocyanation of butadiene can result in the presence of these ligands and their degradation products in the resulting ADN-containing reaction product. If this reaction product is subsequently hydrogenated in the presence of an iron-containing catalyst, the phosphorous may result in a diminution of the useful life of the iron-containing catalyst. There is a need in the art for a process for treating such an ADN-containing reaction product to reduce its ability to diminish the life of the iron-containing catalyst used in the subsequent hydrogenation step.

BRIEF SUMMARY OF THE INVENTION

This need is met by the present invention which is a process for the production of HMD which comprises: (1) reacting butadiene with hydrogen cyanide in the presence of a hydrocyanation catalyst which comprises nickel(0) and a phosphorous-containing ligand to produce a hydrocyanation reaction product that comprises ADN, organic impurities, catalyst, ligand and phosphorous-containing impurities, (2) separating the catalyst and ligand from the hydrocyantion reaction product to make a crude ADN, (3) removing organic impurites from the crude ADN to make refined ADN, (4) contacting the refined ADN with ozone to produce ozone-treated ADN, (5) removing dissolved oxygen from the ozone-treated ADN to produce ozone-treated, deoxygenated ADN and (6) contacting the ozone-treated, deoxygenated ADN with hydrogen in the presence of an iron-containing hydrogenation catalyst to produce a hydrogenation reaction product that comprises HMD.

DETAILED DESCRIPTION OF THE INVENTION

The first step in the present process comprises reacting butadiene with hydrogen cyanide in the presence of a nickel(0) catalyst and a phosphorous-containing ligand. The resulting hydrocyanation reaction product is a mixture of materials including ADN, catalyst, organic impurities, ligand, and phosphorus-containing ligand degradation products. The latter two contain phosphorous. Such a reaction is described in U.S. Pat. Nos. 3,496,215; 3,496,217; 3,496,218; 5,512,696; and 5,821,378, which are incorporated herein by reference.

The next step in the present process comprises separating catalyst and ligand from the hydrocyanation reaction product. A suitable method for accomplishing the separation is extraction, by which the reaction product is mixed with an extracting agent such as cyclohexane, and the resulting mixture is allowed to separate into two phases, with the catalyst and ligand entering the extract phase. The other phase, or raffinate phase, is crude ADN.

The next step in the present process comprises removing organic impurities from the crude ADN to make refined ADN. Typical organic impurities include unreacted 3-pentenenitrile, methylglutaronitrile, and ethylsuccinonitrile. A suitable method for removing such organic impurities is distillation, which produces refined ADN. Despite the removal of the organic impurities, the refined ADN still can contain phosphorus-containing materials which are believed to be ligand degradation products, which are believed to be detrimental to iron-based catalysts which are used to hydrogenate ADN into HMD.

The next step in the present process comprises contacting the refined ADN with gaseous ozone. The reaction conditions are not critical. In general, liquid, refined ADN can be contacted at ambient conditions with air containing greater than 0.1 wt % ozone in a reactor which provides rapid mass transfer rates. However, other conditions of temperature and pressure are acceptable. Suitable reactors are an agitated tank fitted with a gas sparger, a pipeline reactor fitted with a static mixer, a tank fitted with a jet mixer, an absorption column, etc. The ozone gas is transferred to the liquid at a rate that is controlled by mass transfer from the gas to the liquid, the reaction in the liquid phase being essentially instantaneous.

The ozone-treated refined ADN is then flashed to remove the dissolved oxygen. Alternatively, the ozone-treated refined ADN can be sparged with nitrogen or some other nonreactive gas to remove any dissolved oxygen.

The next step in the present process comprises contacting the ozone-treated, deoxygenated ADN with hydrogen and ammonia in the presence of an iron-containing hydrogenation catalyst to produce a hydrogenation reaction product that contains HMD. The hydrogenation of non-ozone treated ADN to produce is described in U.S. Pat. Nos. 3,986,985 and 4,064,172.

While not wishing to be bound by any particular theory, it is believed that phosphorous-containing materials in the hydrocyanation reaction product that contain phosphorous in the +3 oxidation state are injurious to the iron-containing hydrogenation catalyst. It is further believed that the ozone treatment of the refined ADN according to the present invention converts phosphorous in the +3 oxidation state contained therein to phosphorous in the +5 oxidation state, the latter being less injurious to the iron-containing hydrogenation catalyst.

EXAMPLES

Example 1

Effect of P(III) and P(V) Compounds on Fe Catalyst Activity

The purpose of this example is to show that P(III) compounds are stronger poisons than P(V) compounds for Fe catalysts used in the hydrogenation of ADN to HMD. The ADN used in this study was made by a nonhydrocyanation route, so it contained no phosphorous compounds. The hydrogenations were carried out in a 1 liter batch autoclave, to which was added 216 gin of ADN, 216 gm of ammonia solvent, and 2 gm of Fe catalyst. The autoclave was heated to 150 C, at which time it was placed under 5000 psi of pressure with hydrogen. The reaction was allowed to proceed for 20 hrs, at which time the conversion of nitrile groups was measured by gas chromatography. Three runs were made. In the first run no phosphorous compounds were present, in the second experiment the P(III) compound tritolyl phosphite (TTP) was added at a level of $20 \times 10^{18}$ molecules of phosphorous/gm of catalyst, and in the third run the P(V) compound tritolyl phosphate (TTPO) was added at a level of $20 \times 10^{18}$ molecules of phosphorous/gm of catalyst. The percent conversion of nitrile groups for these three runs in shown below:

| Additive | Conversion (%) | Activity Decrease (%) |
|---|---|---|
| none | 74 | 0 |
| TTPO | 59 | 20 |
| TTP | 29 | 60 |

This series of experiments shows that TTP is a more powerful catalyst poison than TTPO, and suggests that the oxidation of TTP to TTPO would lead to longer catalyst runlives.

It is believed that ozone is capable of oxidizing any P(III) compounds present in ADN-containing hydrocyanation reaction product to P(V) compounds, which will reduce the rate of deactivation in the same way as shown above for the model compounds TTP and TTPO.

Example 2

Effect of Ozone Treatment of ADN on Catalyst Deactivation

The ADN used in this example was made by the hydrocyanation of butadiene using a nickel(0) catalyst and a phosphorous containing ligand.

The ADN was refined, as discussed above, and was treated by contacting it with air containing 4.5 wt % ozone at a level of 3.7 mmoles of ozone per kg of ADN. The reaction was run at ambient conditions and with a liquid hold up time in the reactor of 15 minutes. The reactor was a continuous stirred reactor fitted with a turbine agitator to give good mass transfer.

Hydrogenation of the ADN was carried out in a continuous adiabatic trickle bed reactor that contained Fe-based catalyst. The reactor was fed a mixture of ADN, ammonia and hydrogen at a pressure of 250 bars. The inlet temperature to the reactor was adjusted to maintain the conversion of ADN at 99.9%. As the catalyst deactivates it is necessary to gradually increase the inlet temperature to maintain the conversion of ADN at the 99.9% level. The deactivation rate is determined by the rate at which the inlet temperature needs to be increased, in units of degrees Centigrade per 100 hours of operation.

The reactor was started up on ADN that was not ozone treated, and the deactivation rate was measured to be 3 degrees Centigrade per 100 hrs of operating time. The feed was then switched to ADN that had previously been ozone treated. This ADN was the same material that had been used in the earlier part of the hydrogenation study, except that it had been ozone treated. This ADN was fed for a period of 275 hrs, during which time the deactivation rate was 1 degree Centigrade per 100 hrs of operating time. The ADN feed was then switched back to the original untreated material, and the deactivation rate increased to 3 degrees Centigrade per 100 hrs operation. This data indicates that ozone treatment of ADN causes the rate of deactivation of the Fe catalyst to decrease by a factor of three.

What is claimed:

1. A process for the production of HMD which comprises: (1) reacting butadiene with hydrogen cyanide in the presence of a hydrocyanation catalyst which comprises nickel(0) and a phosphorous-containing ligand to produce a hydrocyanation reaction product that comprises ADN, organic impurities, catalyst, ligand and phosphorous-containing impurities, (2) separating the catalyst and ligand from the hydrocyantion reaction product to make a crude ADN, (3) removing organic impurites from the crude ADN to make refined ADN, (4) contacting the refined ADN with ozone to produce ozone-treated ADN, (5) removing dissolved oxygen from the ozone-treated ADN to produce ozone-treated, deoxygenated ADN and (6) contacting the ozone-treated, deoxygenated ADN with hydrogen in the presence of an iron-containing hydrogenation catalyst to produce a hydrogenation reaction product that comprises HMD.

2. The process of claim 1 in which the phosphorous-containing impurities comprise compounds that contain phosphorous in the +3 oxidation state.

* * * * *